United States Patent [19]

Liu et al.

[11] Patent Number: 5,228,960
[45] Date of Patent: Jul. 20, 1993

[54] ANALYSIS OF SAMPLES BY CAPILLARY ELECTROPHORETIC IMMUNOSUBTRACTION

[75] Inventors: Cheng-Ming Liu; Hann-Ping Wang, both of Yorba Linda; Fu-Tai A. Chen, Brea; James C. Sternberg, Fullerton; Gerald L. Klein, Orange, all of Calif.

[73] Assignee: Beckman Instruments, Inc., Fullerton, Calif.

[21] Appl. No.: 916,313

[22] Filed: Jul. 17, 1992

[51] Int. Cl.⁵ .............................................. C25B 7/00
[52] U.S. Cl. .................................................. 204/182.8
[58] Field of Search ...................... 204/182.8, 299 R; 436/516

[56] References Cited

U.S. PATENT DOCUMENTS

| | | | |
|---|---|---|---|
| 4,668,363 | 5/1987 | Gebott et al. | 204/182.8 |
| 5,120,413 | 6/1992 | Chen et al. | 204/180.1 |

FOREIGN PATENT DOCUMENTS

| | | | |
|---|---|---|---|
| 0280570 | 12/1986 | Japan | 436/516 |

OTHER PUBLICATIONS

Aguzzi, F. et al., "Immunosubtraction Electrophoresis: A Single Method for Identifying Specific Proteins Producing the Cellulose Acetate Electropherogram." Estratto dal. Boll. 1st Sieroter, Milanese 56/3: 212-216 (1977) (published in English).

White, W. A. & Attwood, E. C. "Immunofixation and Immunosubtraction on Agarose Gel: An Acid in Typing of Monoclonal Gammopathies." Biochem. Clin. 10:571-574 (1986).

Merlini, G. et al., "Identification of Specific Plasma Proteins Determining the Agarose Cel Electrophoresis by the Immunosubtraction Technique." *J. Clin. Chem. Biochem.* 21:841-844 (1983).

Beckman Bulletin EP-6 "High Resolution Electrophoresis in the Detection of Monoclonal Gammopathies and Other Serum Protein Disorders." (1990).

Beckman Bulletin EP-3 "Paragon ® Serum Protein Electrophoresis II (SPE-II) Applications Guide" (1990).

Beckman Bulletin EP-2. "Immunoelectrophoresis Applications Guide." (1991).

Beckman Bulletin EP-4 "Immunofixation Electrophoresis Applications Guide." (1991).

Beckman Instructions 015-246513-H "Paragon ® Electrophoresis System-IFE" (1990).

Sun, T. et al. "Study of Gammopathies with Immunofixation Electrophoresis." AJCP 72/1: 5-11 (1979).

Beckman Bulletin D5-823 "Increased Sensitivity with Capillary Electrophoresis." (1992).

Beckman Instructions 015-246346-B "Paragon ® Immunofixation Electrophoresis" (1986).

*Primary Examiner*—John Niebling
*Assistant Examiner*—Cybille Delacroix-Muirheid
*Attorney, Agent, or Firm*—William H. May; Arnold Grant

[57] ABSTRACT

Disclosed herein are methodologies for the Capillary Electrophoretic Immunosubtraction ("CEI") of samples. In a preferred embodiment, CEI of a sample comprising constituent parts to be separated comprises the steps of: (1) separating a first aliquot of the sample into constituent parts by capillary electrophoretic techniques, and detecting said parts; (2) admixing a second aliquot of said sample with at least one specific binding partner to a constituent of said sample, said specific binding partner capable of being substantially removed from said aliquot; (3) separating said second aliquot into constituent parts by capillary electrophoretic techniques and detecting said parts; and (4) comparing the separated constituent parts of step (3) with the separated constituent parts of step (1).

17 Claims, 5 Drawing Sheets

ANALYSIS OF SAMPLES BY CAPILLARY ELECTROPHORETIC IMMUNOSUBTRACTION

FIELD OF INVENTION

The present invention is generally directed to the analysis of samples and more specifically to the analysis of samples using capillary electrophoretic techniques. In a particularly preferred embodiment, the invention is directed to the analysis of clinical samples by capillary electrophoretic immunosubtraction.

BACKGROUND OF THE INVENTION

"Immunoglobulins" ("Ig") are antibodies which consist of a pair of two "heavy" chains linked to a pair of two identical "light" chains; the hypothetical structure of the immunoglobulin is in the shape of a "Y" with the heavy chains forming the base of the Y, and the light chains forming the two branches. The heavy chains and light chains are separately synthesized by the immune system; such synthesis is synchronized by the immune system, such that under normal circumstances, complete immunoglobulins are produced.

Immunoglobulins are important to humans with respect to the mediation of immunity; i.e., the chains of immunoglobulins comprise antigen binding sites such that when a foreign antigen is introduced into a human host, activated B-cells synthesize Igs with specificity for the antigen. The immunoglobulins are then capable of specifically binding to the invading antigen, whereby the host can effectively mediate the removal thereof from the body.

There are two types of light chains, referred to as "kappa" and "lambda". There are several types of heavy chains and the classification of the immunoglobulins are predicated upon the heavy chain type. I.e., immunoglobulins comprising gamma ("$\gamma$") heavy chains are designated as "IgG"; alpha ("$\alpha$"), IgA; mu ("$\mu$"), IgM; delta ($\delta$), IgD; and epsilon ($\epsilon$) IgE.

Immunoglobulins are proteins; thus, they are comprised of amino acid sequences. Within the specific isotype of immunoglobulin, the amino acid sequences for the light chains are substantially identical, and the amino acid sequences for the heavy chains are substantially identical. Thus, using IgG as an example, approximately one-half of the light chains and three-fourths of the heavy chains have amino acid sequences that are identical from one IgG molecule to the next. The region of identical amino acid sequences is referred to as the "constant region". The remaining one-half of the IgG light chain and one-fourth of the heavy chain are composed of highly variable amino acid sequences, referred to as the "variable region". The variable regions are important in that these give rise to "antigen binding sites" i.e. the regions that bind with specificity to particular antigens. Thus, changing the amino acid sequence in a variable region produces immunoglobulins with different antigen binding sites.

This capability is of critical importance to the immune system, and hence survival, of, e.g., mammals, including humans. Antigens typically have several different "epitopes" i.e., regions to which antibodies can bind. Thus, an immunoglobulin that has a variable region specific for one epitope on the antigen will typically be unable to bind to a different epitope on that antigen; therefore, the immune system, when stimulated, will produce a variety of immunoglobulins that have different variable regions which are specific for different antigen epitopes. This is referred to as a "polyclonal immune response," i.e., a variety of immunoglobulins are secreted by the activated B-cells in response to antigenic stimulation.

The immune system is regulated such that upon stimulation, the B-cells will produce more than a sufficient amount of immunoglobulins to neutralize the invading antigen; thereafter, B-cell production of the immunoglobulins ceases in that the need for the immunoglobulins secreted in response to the antigen is negated or dissipated.

Occasionally, single, unregulated B-cell clones will continue to produce immunoglobulin of the same idiotype (i.e., identical in terms of antigen binding site). This results in at least two problems which impact on the immune system of the host: first, the proliferation and subsequent accumulation of such immunoglobulins can stimulate the production of antibodies directed thereto (which can be referred to as an "autoimmune response"); and second, the immune system is severally "strained" by the need to attack the accumulating immunoglobulins such that the ability to fight invading antigens is weakened. Immunoglobulins of the same idiotype produced by single, unregulated B-cell clones are referred to as "monoclonal gammopathies". Monoclonal gammopathies are of principal importance with respect to clinical disorders.

Monoclonal gammopathies do not necessarily cause clinical disorders in an individual. Such a situation can be referred to as "benign monoclonal gammopathy" or "monoclonal gammopathy of undetermined significance". However, many clinical disorders are associated with monoclonal gammopathy. For example, monoclonal IgM (i.e. an increase in the production of an IgM idiotype by unregulated B-cell clones) is associated with the disease Waldenström's macroglobulinemia. Because IgM has a (relatively) high molecular weight, an increase production thereof is associated with an increase in the viscosity of the macroglobulinemia patient's blood, referred to as "hyperviscosity". Hyperviscosity is associated with, e.g., headache, dizziness and vertigo.

Multiple myeloma is associated with an increase in IgG, IgA, IgD or IgE idiotypes, as well as kappa or lambda light chains, or gamma, alpha, mu or delta heavy chains. A major pathologic feature of multiple myeloma is bone destruction, i.e., bone deformity or acute, painful pathological fractures. Clinically, the patient may experience bone pain, infections due to decreased production of normal Ig's, and anemia. Twenty percent of myeloma patients evidence Bence Jones protein, which is a free monoclonal light chain; these light chains, because of their (relative) small size are typically excreted, and hence present, in patient urine. Multiple myeloma can also impact neural tissue (i.e., the spinal cord, nerve roots and cranial or peripheral nerves).

As is apparent, information regarding monoclonal gammopathies is of clinical value and importance to the understanding of a variety of severe and debilitating disease states. It is therefore essential that procedures be available for the identification of monoclonal gammopathies (hereinafter "MG"). Two well-known procedures for the analysis of MG are Immunoelectrophoresis ("IEP") and Immunofixation Electrophoresis ("IFE"). Both procedures are more similar than dissimilar in protocol, although interpretation of IFE results is somewhat easier compared to IEP.

IFE is a two stage procedure using agarose gel protein electrophoresis in the first stage and immunoprecipitation in the second. In a clinical setting for the determination of MG, a clinical sample (e.g., whole blood, serum, plasma, urine, cerebro spinal fluid) is placed in multiple positions ("lanes") on an agarose gel. Because immunoglobulins are proteins, they have a charge distribution such that when an electric field is applied to the gel-containing sample, immunoglobulins will traverse the gel from anionic to cationic electrode Thereafter, antisera comprising antibodies to specific immunoglobulin classes (typically IgG, IgA, IgM, kappa and lambda) are applied to specific lanes. The gel and antisera are incubated, during which time immune complexes between specific immunoglobulins and the antibodies thereto are formed. Staining solutions are then utilized to indicate the location of such immune complexes—if no MGs are present, a somewhat consistent color stain will be evidenced; if MGs are present, these will accumulate in specific regions on the gel (due to their inherent identical weight and charge) such that a color band will appear. By utilizing a reference pattern on the gel, one can then determine the MG type present on the gel. FIG. 1 provides a patient sample evidencing an IgG (lambda) monoclonal protein as identified by IFE (each of the designated headings refer to the particular antiserum applied to that lane).

The PARAGON ® electrophoresis system is a commercially available system for conducting both IFE and IEP. PARAGON ® is a registered trademark of Beckman Instruments, Inc., Fullerton, Calif., U.S.A. See also, U.S. Pat. No. 4,669,363 which is incorporated herein by reference.

IFE can be considered a "positive indicator" test. I.e., the presence of a particular band is indicative of the presence of an MG corresponding to a particular immunoglobulin type. A technique related to IFE which can be considered a "negative indicator" test is referred to as Immunosubtraction Electrophoresis ("ISE"). ISE, in essence, reduces by one the number of steps of IFE. In ISE, the sample can be mixed with, e.g., an insolubilized antibody directed to an immunoglobulin; if present, that immunoglobulin will bind to the insolubilized antibody and is thus "removed" from the sample. Therefore, the sample is applied to a gel, subjected to electrophoresis, and a coloring stain is applied. In a "normal" sample, the stain should be relatively consistent across the gel; in an "abnormal" sample, i.e., one that includes MG, the stain will be absent from a region on the gel, owing to the removal of that monoclonal immunoglobulin in the initial step. Thus, the absence of a particular band is indicative of the presence of the corresponding MG from the sample, hence the "negative indicator" designation.

IEP, IFE and ISE all require the use of a separation gel as well as signal-generating stains. These procedures all involve multiple steps. Thus, the procedures can be somewhat labor intensive, which can decrease throughput, an obvious impediment in a clinical setting. Additionally, there may be a concern with the amount of disposable end-products associated with these procedures—each sample requires a gel which must be properly disposed, particularly when the analysis involves clinical samples. Such a disposal scenario can further increase the allied costs associated with these procedures.

As noted, immunoglobulins are proteins which can be separated from each other using gels subjected to an electric field. Proteins, including those from clinical samples, can also be analyzed using capillary zone electrophoresis ("CZE"). See, for example, Chen, Fu-Tai A., et al. "Capillary Electrophoresis—A New Clinical Tool." *Clin. Chem.* 77/1:14-19 (1991); see also, U.S. Pat. No. 5,120,413. Both of these documents are incorporated herein by reference.

Capillary zone electrophoresis is a technique which permits rapid and efficient separations of charged substances. Separation of the constituents of clinical samples can typically be accomplished in less than 20 minutes, typically in less than 10 minutes. In general, CZE involves introduction of a sample into a capillary tube, i.e. a tube having an internal diameter of from about 2 to about 2000 microns ("$\mu m$"), and the application of an electric field to the tube. The electric potential of the field both pulls the sample through the tube and separates it into its constituent parts. I.e., each of the sample constituents has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel. Separation of the constituents in the sample is predicated in part by the size and charge of the constituents travelling through the gel matrix. Gel CZE has several disadvantages, notably, the unpredictability of the gel material. I.e., such gels eventually "breakdown" or can only be used for limited analytical runs. Such unpredictability is unacceptable in any setting where numerous analytical runs are conducted.

In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (i.e., the buffer solution and the sample being analyzed), must also flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based electrophoresis.

Fused silica is principally utilized as the material for the capillary tube because it can withstand the relatively high voltage used in CZE, and because the inner walls ionize to create the negative charge which causes the desired electroendosmatic flow. However, alumina, beryllium, Teflon ®-coated materials, glass, quartz and conbinations of these (with or without fused silica) can also be utilized. The capillary column is typically capable of withstanding a wide range of applied electrophoretic fields of between about 10 volts per centimeter ("v/cm") up to about 1000 v/cm. The capillary column may be coated on the outside (using, e.g., a polyimide material) for ease of handling. The inner wall of the capillary may be untreated or coated with a material capable of, inter alia, reducing adsorption to the inner wall during electroendosmatic flow of the bulk solution. However, it is typically preferred that the inner wall be uncoated because typical coatings have a tendency to breakdown in an unpredictable manner. In U.S. Pat. No. 5,120,413, analysis of clinical samples was conducted using untreated capillary columns.

The results of CZE analysis are typically presented as "electropherograms", i.e., peaks of various widths and heights which correspond to the constituent parts of the sample. For example, a constituent which is present in a sample in a high concentration may evidence a peak having a large height and wide width compared to a constituent present in a (relative) low concentration. Typically, the electropherogram is derived by plotting detection units (typically ultraviolet light absorbance) on the vertical axis, and time of constituent traversal through the column to a detection region on the horizontal axis. Results can also be derived in terms of a unit value, typically derived from the areas bounded by the individual peaks.

Open CZE has many desirable qualities for, e.g., clinical sample analysis: because the analysis does not involve a gel-filled column, the inherent limitations on the number of analytical runs that can be conducted with any particular gel-filled column are avoided; when the capillary column is untreated, the aura of unpredictability which can be associated with coated columns is avoided; the sample size is small (usually on the order of 5 to 200 μl of diluted sample); sample analysis time is fast, i.e. less than about 20 minutes; and the protocol lends itself to automation, thus decreasing the labor skills necessary for efficient and effective sample analysis.

What is needed, then, is a technique applicable to the analysis of monoclonal gammopathies which can provide results with a minimum of processing steps; which is easy to utilize; which provides for high throughput; and which avoids the end-product disposal problem occasioned by the use of separating gels.

SUMMARY OF THE INVENTION

The disclosed invention satisfies these needs. In accordance with the invention, a capillary electrophoretic immunosubtractions method is disclosed. Preferably, capillary electrophoretic immunosubtraction ("CEI") of a sample comprising constituent parts to be separated comprises the steps of: (1) separating a first aliquot of the sample into constituent parts by capillary electrophoretic techniques, and detecting said parts; (2) admixing a second aliquot of said sample with at least one specific binding partner to a constituent of said sample, said specific binding partner capable of being substantially removed from said aliquot; (3) separating said second aliquot into constituent parts by capillary electrophoretic techniques and detecting said parts; and (4) comparing the separated constituent parts of step (3) with the separated constituent parts of step (1).

Preferably, the sample is a clinical sample and the constituent parts include immunoglobulins whereby the specific binding partner is an anti-immunoglobulin antibody. Most preferably, the specific binding partner is either insolubilized before the second aliquot is admixed therewith, or is capable of being insolubilized after admixture with the aliquot.

Preferably, the detection of the constituent parts is such that the results are presented as electropherograms, whereby that the comparison is between electropherograms. If the sample comprises a constituent of interest, for example, a monoclonal immunoglobulin, the first electropherogram will evidence the "complete" constituent profile of the sample; after admixing an aliquot of the sample with a specific binding partner for a desired immunoglobulin, and separating the bound complex from the sample, the second electropherogram, when compared to the first, will evidence a "subtracted" peak corresponding to the immunoglobulin separated from that aliquot. In this scenario, then, the absence of a peak can indicate that the sample in question comprises a monoclonal immunoglobulin, which can both be identified and quantified.

DETAILED DESCRIPTION OF PREFERRED EMBODIMENTS

Figure 1:
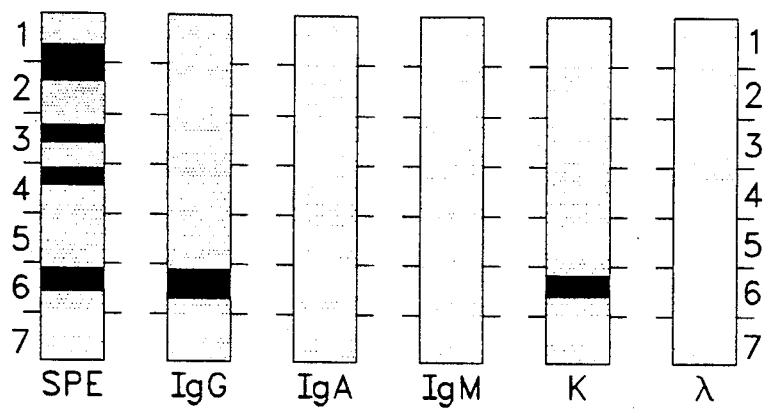
FIG. 1 is an example of an IFE gel resulting from analysis of an IgG kappa sample.

The specificity of binding associated with antibodies and their receptive antigenic binding partner(s) has been extensively utilized in the arena of clinical diagnoses. Immunoelectrophoresis, Immunofixation Electrophoresis and Immunosubtraction Electrophoresis, as described above, are exemplary. In clinical settings, modern medicine has both driven and followed two important trends: the need for (a) rapid and (b) detailed, accurate information regarding the medical status of a patient. Additionally, it is not unusual to read or hear on a daily basis of the increasing costs associated with health care; an increasing populace with increasing health care demands, coupled with the above trends, has necessitated continued improvement in the manner in which diagnostic evaluation are provided.

Determination of monoclonal gammopathies is critical for both evaluation and treatment purposes. While the need for accurate results should not be compromised in terms of the speed in obtaining such results, any protocol which allows for obtaining accurate clinical information rapidly is desirable. Capillary Electrophoretic Immunosubtraction ("CEI"), as disclosed herein, is such a protocol. CEI uniquely exploits both the speed of capillary electrophoresis and the specificity of immunological reactions involving antigens and antibodies—significantly, CEI avoids the need for slab gels associated with IEP, IFE and ISE.

CEI of a sample comprising at least one constituent part to be analyzed comprises the steps of:

(1) separating a first aliquot of the sample into constituent parts by capillary electrophoretic techniques, and detecting said parts;

(2) admixing a second aliquot of said sample with at least one specific binding partner capable of being substantially removed from said aliquot;

(3) separating said second aliquot into constituent parts by capillary electrophoretic techniques, and detecting said parts; and (4) comparing the separated constituent parts of step (3) with the separated consistent parts of step (1).

As used herein, the term "substantially removed" does not necessarily imply physical removal; rather the term is meant to indicate that the specific binding partner is not included in the separation of step (3).

Preferably, the aliquots of steps (1) and (2) are approximately the same value amounts obtained from the sample at approximately the same time period under the same condiments. I.e, those skilled in the art will readily appreciate necessary variables can be avoided when aliquots from the same sample are obtained using approximately the same parameters for each.

As noted, capillary electrophoresis techniques have been utilized for the separation of the constituent parts of clinical samples. Typically, such separation can be accomplished in less than about 10 minutes, although longer or shorted time periods can be utilized. By convention, in a clinical setting, rapidity of analysis is desirable in terms of deriving faster results and increased throughput. However, the time of analysis is a variable which is determined vis-a-vis the needs and objectives of the investigator. Those skilled in the art are credited with varying the capillary electrophoretic conditions so as to derive appropriate separation times; typically, by increasing the applied voltage, separation time decreases, and vice-versa.

The capillary column utilized for the separation can be untreated (i.e. the inner walls are "bare" fused silica or the like) or coated with an appropriate material. Coated capillaries have enjoyed widespread use in the area of capillary electrophoresis, principally because these coatings tend to limit protein absorption to the untreated walls during the electrophoretic separation procedure. However, eventually these coatings will "break-down", and this can happen in an unpredictable manner. Therefore, while the disclosed CEI protocol can be used with either untreated or coated columns, it is preferred that the columns be untreated. When untreated capillary columns are utilized, preferably the separation buffer is as disclosed in U.S. Pat. No. 5,120,413. Most preferably, the buffer is 150 mM borate, pH 10.00±0.25; concentrations between about 70 mM and about 400 mM are, however, viable. As those in the art appreciate, as the molarity of the buffer increases, the temperature inside the column can increase; thus, in situations where temperature effects upon the constituents are a factor, lower concentrations of the buffer should be utilized. Specific details regarding appropriate buffers are disclosed in the aforementioned document, which is incorporated herein by reference. However, it is to be understood that the disclosed CEI protocol can be accomplish with any separation buffer used in conjunction with the separation of proteinaceous materials using coated or untreated columns.

The first step of the CEI protocol is intended to provide "baseline" or "control" results. Focusing on electropherograms, the electropherogram derived from the separation of the first aliquot will evidence the presence of a variety of proteinaceous materials within the clinical sample, including, if present, the presence of abnormal immunoglobulin concentration. However, in and of itself, such results are typically insufficient to allow for evaluation with a view towards identification of the gammopathy.

Beneficially, antibodies directed to specific immunoglobulins can be utilized to "pull" particular immunoglobulins from the aliquot. For example, if the sample is being analyzed to determine if IgA monoclonal gammopathy is present, admixing an aliquot of the sample with anti-human IgA antibodies results in an appropriate immunological reaction—the IgA from the sample binds to the anti-IgA antibodies, thus forming a conjugate. By insolublizing the conjugate, or in the substantially equivalent alternative, by initially utilizing insolubilized anti-IgA antibodies, the conjugate internally separates from the aliquot by "settling" due to the inherent density differences. Thus, the IgA has been "subtracted" from the aliquot such that when this aliquot is analyzed by capillary electrophoretic techniques, the resulting electropherogram will not evidence a peak which originally corresponded to IgA.

In order to compare the two electropherograms (or the comparative areas beneath the peaks), it is preferred that the electropherograms be normalized, i.e. variations between the conditions of the first run and the second run are adjusted such that direct comparisons between the different separations can be conducted. Typically, normalization involves three steps: (1) baseline normalization; (2) absorbance normalization; and (3) time normalization.

Baseline normalization is typically accomplished by adjusting the electropherograms such that each has a common horizontal baseline; beneficially, this merely requires shifting upwards or downwards the entire electropherogram in the case where the initial baseline is below or above the zero axis, respectively. Baseline normalization allows for creation of a common horizontal axis.

Absorbance normalization is preferably based upon the most prevalent protein component in serum, albumin. Typically, the electropherogram peak associated with albumin is the "tallest" peak. By selecting a single absorbance maximum for the albumin peak, all of the peaks within the electropherogram will be adjusted relative thereto. Absorbance normalization rectifies differences in, e.g. the amount of aliquot analyzed during the first and second runs. For example, if the second aliquot has a higher volume compared to the first, the proportional proteins in the second aliquot will be greater relative to the first; thus, the peaks of the second electropherogram will be artificially different relative to the corresponding peaks of the first electropherogram. Accordingly, absorbance normalization is established by selecting an absorbance maximum for, e.g. albumin; is established; if the albumin peak is above that value, then all of the peaks in that electropherogram are adjusted downward, proportionally, to the degree that the albumin peak is adjusted downwards. The opposite scenario occurs when the albumin peak is lower than the absorbance maximum. As those in the art will appreciate, because the adjustment is conducted in proportionally the same manner for all of the peaks (relative to the adjustment of the albumin peak vis-a-vis the predesignated absorbance maximum), the areas beneath each peak, relative to each peak in the electropherogram, remain the same. Preferably an absorbance maximum for albumin is between about 0.10 and about 0.20 absorbance units (in thousands), most preferably about 0.15. It is to be understood the absorbance normalization can be accomplished by the utilization of an external marker, i.e. a material added to the sample which traverses the column along with the sample constituents. Additionally, constituent parts other than albumin are applicable.

Time normalization is principally accomplished in order to place the resulting electropherogram results within a constant region. Preferably, this is accomplished by the use of two "markers" which are added to the sample prior to the analysis of the two aliquots, the markers being capable of traversing the capillary column and being detected within the approximate same time period as the sample constituents are detected. Methodologies for utilization of at least two external markers which can traverse the capillary column prior to and after the constituent species, and protocols for selecting such markers to travel in this fashion are disclosed in U.S. Ser. No. 07/708,424, filed on May 31, 1991 by Fu-Tai A. Chen, entitled "Identification of Sample Constituents Utilizing Capillary Electrophoresis", which is incorporated fully herein by reference. In essence, because approximately the same concentration of the markers are analyzed in both aliquots (due to addition thereof to the original sample), the markers traverse the capillary, and hence are detected, at approximately the same times. I.e., the first marker in each aliquot will be detected at approximately the same time and the second marker in each aliquot will be detected at approximately the same time, preferably with the separated constituents appearing between the first and second markers. Thus, to the degree that the detected sample constituents are detected at different times (due to, e.g., increased amounts and hence of concentrations of the second aliquot versus the first), the relative detection times of the two sets of constituents can be normalized using the markers. As those skilled in the art will recognize, time normalization, like absorbance normalization, is accomplished such that the relative areas beneath the individual electropherogram peaks remain the same; such normalization merely allows the two electrophorograms to be accurately compared to each other.

Most preferably, the two markers are prepared as follows: 20 mg of dichlorobenzoic acid is dissolved into 40 µl of benzyl alcohol and this mixture is added to 100 ml of an appropriate buffered solution, such as ICS ™ diluent (Beckman Instruments, Inc.). From this admixture, an appropriate amount is added to the sample— thus, equivalent aliquots taken from the sample will comprise approximately the same relative concentrations of the markers. During analysis, these markers traverse the column along with the sample constituents, i.e. the electrophoretic mobilities of the markers determines the "speed" of traversal. For the most preferred markers, the electrophoresis mobilities are such that on the electropherogram, the dichlorobenzoic acid peak will appear (typically) as the "first" detected peak, followed by the sample constituents, then followed by the "last" detected peak, benzoyl alcohol. Thus, the peaks attributed to the sample constituents are "bound" by the two markers.

The specific binding partner to the constituent of interest, e.g., a monoclonal immunoglobulin, can be soluble or insoluble; preferably, the binding partner is insoluble in that after admixture with the second aliquot, the insolubilized immunoconjugate will have a tendency to settle at the bottom of a reaction vessel; this facilities ease of removal of a portion of the second aliquot for analysis. When the binding partner is soluble, it is preferably capable of being insolubilized. I.e., the binding partner can include, e.g., a biotin "hook" which can then bind to insolubilized avidin, or the binding partner can be insolubilized by use of an insolubilized material capable of binding to the binding partner. Those in the art are credited with the ability to select appropriate conditions and components for insolubilizing a soluble specific binding partner.

The ratio of the specific binding partner to the sample constituent of interest is principally selected with respect to two factors: (1) the ability to remove substantially all of the constituent of interest from the sample; and (2) loading efficiency of the binding partner onto a solid support, i.e. the ability to substantially maximize the amount of binding partner which can effectively bind to the constituent. In essence, the second factor can be viewed as one motivated by cost:benefit—overloading the binding partner can increase cost without increasing the amount of constituent binding. It is to be understood, therefore, that the ratio of specific binding partner to constituent of interest can be 1:1.

Focusing on the immunoglobulins IgA, IgM and IgG, normal ranges for these in serum are as follows: 69-382 mg/ml; 63-277; and 723-1685. However, a sample can evidence an abnormality even if the concentration of, e.g., IgG is 1000 mg/ml, if monoclonal IgG is present. With respect to heavy chain immunoglobulins (IgG; IgM; IgA; IgE; IgD), a preferred analytical ratio of anti-heavy chain immunoglobulin antibody to immunoglobulin is between about 1:1 and about 1:15; more preferably between about 1:4 and about 1:10, and most preferably 1:6. For light chain immunoglobulin (lambda; kappa), a preferred analytical ratio of anti-light chain antibody to immunoglobulin is between about 1:1 and about 1:15; more preferably between about 1:6 and about 1:14; and most preferably about 1:12. The differences between preferred ratios vis-a-vis heavy and light chains is primarily based upon loading of the antibodies onto the solid support (more anti-light chain antibody is typically required to maximize light chain binding, relative to the heavy chains). However, in both cases, these ratio ranges provide sufficient antibody to react with the immunoglobulin of interest such that substantially all of the particular immunoglobulin will be "removed" from the second aliquot.

It is preferred that the clinical sample be diluted prior to analysis; such dilution, facilitates inter alia, achieving a desired analytical ratio, and further aids in utilization of the sensitivity associated with capillary electrophoresis analysis. I.e., non-dilution of a clinical sample, particularly serum, can provide too much protein component such that analysis is difficult. Focusing on serum, a most preferred dilution is a one part serum to ten parts of an appropriate diluent; dilution up to one part serum to 100 parts diluent can be utilized. The diluent is preferably a lightly buffered saline solution, pH 7.0; such a diluent will not impact upon the sample in a deleterious manner. A preferred diluent is the ICS ™ diluent. Of the 1:10 dilution, it is most preferred that 10 µl thereof be added to 100 µl of a "slurry" which comprises the insolubilized specific binding partner. The slurry is comprised of, most preferably, 50% of a "gel suspension" and, most preferably, 50% of the same diluent used in the dilution of the sample. The gel suspension consists of the insolubilized specific binding partner.

The solid support can be any material applicable to diagnostic assays—these are well known and will not be set forth herein in detail. Exemplary materials include microparticles which contain one or more of the following: free hydroxyl group; free amino group; free thiol group; and carboxylic acid that is capable of being activated. As those in the art appreciate, these groups allow for direct protein conjugation (or protein "loading"). Additionally, the solid support can be loaded with, e.g., avidin (or a derivative thereof) when a "Universal Solid Support" is utilized. A Universal Solid Support comprises a binding partner which will bind to a specific material which is coupled to an anti-immunoglobulin antibody. For example, a Universal Solid Support comprising avidin can be utilized in conjunction with biotinylated anti-immunoglobulin antibodies; such a support is preferred principally from a manufacturing position in that a single support can be produced for use in conjunction with, e.g. biotinylated anti-IgA antibodies and biotinylated anti-IgM antibodies.

The selection of a particular solid support is discretionary with the investigator. Preferably, the solid support is cyanogen bromide activated Sepharose ™ (Pharmacia). Anti-human immunoglobulin (heavy or light chain) antibodies are commercially available; typically the source is rabbit, although any non-human species can be utilized for derivation of the antibodies. DACO Co. is exemplary of commercial sources of rabbit anti-human immunoglobulin antibodies. Beneficially, these antibodies can be coupled directly to the aforementioned solid support. With respect to IgG, a preferred solid support is agarose coupled Protein G (Isolab). As those in the art appreciate, Protein G is a cell surface protein isolated from group G Streptococcus which specifically binds to IgG from a number of mammals, including humans. However, anti-human IgG antibodies can be utilized with substantially equivalent efficiency.

Preferably, the gel suspension is prepared by admixing 1.0 g. of solid support with 10.5 ml of hydrochloric acid; swelling of the support occurs such that about 3.5 ml of gel suspension is available. For heavy chain immunoglobulins, it is most preferred that 5 mg. thereof is added to 1 ml of the gel and 1 ml of the aforementioned diluent (i.e., 2.5 mg/ml gel suspension); for light chain immunoglobulins, it is most preferred that 10 mg. thereof is added to 1 ml of the gel and 1 ml of the aforementioned diluent (i.e. a 5.0 mg/ml gel suspension). As noted, most preferably, 10 μl of the diluted sample is admixed with 100 μl of gel slurry; these values provide the most preferred anti-human-imnunoglobulin antibody: immunoglobulin ratios of 1:6 (heavy chain) and 1:12 (light chain). Those skilled in the art are credited with the ability to adjust the aforementioned concentrations in order to derive ratios other than the particularly preferred ratios delineated herein. Again, the ratios are principally selected to maximize binding while minimizing the amount of antibody utilized. The aforementioned detail is not to be construed as a critical feature of the invention in toto but rather as an indication of how the skilled artisan can select a desired analytical ratio.

Comparing the separated constituent parts of the first aliquot and the second aliquot can be accomplished in a variety of substantially equivalent ways. Preferable, the comparison is visually oriented, i.e. the normalized electropherograms are directly compared such that a "subtracted" peak can be readily identified. The areas beneath each constituent peak can also be compared; i.e. with the exception of the area beneath "subtracted" peak, the numerical area values beneath the individual peaks from the first and second aliquots are substantially the same, while the numerical area beneath the region of the immunosubtracted immunoglobulin from the second aliquot will be substantially different than the corresponding area for the first aliquot. An alternative approach to the analysis, which is also visually oriented, is based upon the manner in which slab-gel IFE results are derived, i.e. bands at the location of the monoclonal gammopathy. Methodologies are apparati for converting electropherogram peaks into such bands are disclosed in co-pending U.S. Ser. No. 07/911,307 entitled "Method and Apparatus for Displaying Capillary Electrophoresis Data" by Gerald L. Klein and Steven P. Katzman, which is incorporated herein by reference.

Capillary electrophoresis systems which can be utilized in conjunction with the CEI procedure disclosed herein are well known and varied. A particularly preferred instrument is a multi-channel apparatus which allows for the simultaneous evaluation of at least two different aliquots of the sample; more preferably, the apparatus has the capability of analyzing a plethora of aliquots simultaneously such that different anti-immunoglobulin antibodies can be utilized whereby the resulting electropherograms are normalized and compared. By utilizing such multichannel analysis, identification of the presence of monoclonal gammopathy(ies) from a variety of possibilities (i.e., IgG, IgA, IgM, and kappa and lambda) can be rapidly achieved after a single analytical evaluation of the sample. A particularly preferred capillary electrophoretic system is disclosed in co-pending U.S. Ser. No. 07/916,308 entitled "Multichannel Automated Capillary Electrophoresis System" by Gerald L. Klein, which is incorporated herein by reference. For research evaluation and validation, a particularly preferred capillary electrophoretic system is the P/ACE ™ high performance capillary electrophoresis system (Beckman Instruments, Inc.). Such instruments are most preferred in that normalization of the eletpherograms can be accomplished via on-board computer software.

EXAMPLES

The following examples directed to preferred embodiments of the invention disclosed herein are not intended, nor should they be construed, as limiting the disclosure, or the claims to follow. For purposes of brevity, the examples focus serum on clinical samples; however, the disclosed capillary electrophoretic immunosubtraction technique is not limited to clinical samples.

I. MATERIALS AND METHODS

A. Materials

1) Capillary Electrophoresis Procedures

Capillary electrophoresis of clinical samples was performed on a Beckman Instruments, Inc. high performance capillary electrophoresis system (Beckman Instruments, Inc., Fullerton, Calif., U.S.A., Model No. 357575). Data analysis was performed on System Gold ® software (Beckman Instruments, Inc.). The aforementioned capillary electrophoresis system contains built in 214, 254, 280 and 415 nm narrow band filters for on-line detection- The optics module and detector included a deuterium lamp (ultraviolet) light source; the 214 nm filter was utilized for detection. The aforementioned system also has the capability of laser-induced fluorescence (LIF) detection (Beckman Instruments, Inc., Model No. 477125; includes argon ion 488 nm laser, 520 nm emission filter). Electrophoresis was performed in an externally coated (polyimide) fused silica tube, 27 µm i.d. and 20 cm long. The detection window is located approximately 6.5 m from the column outlet.

Clinical samples were placed on the inlet tray of the above-described capillary electrophoresis system. Samples were automatically injected into the capillary tube by the pressure injection mode (10 sec. at 5 psi). Sample separations were performed in less than about 10 minutes using a separation voltage of 10 KV (voltage gradient of 370 volts/cm). The capillary tube was washed and reconditioned between runs (60 seconds, 1.0N NaOH; 60 seconds, deionized water). On-line temperature was 24° C.

2) Electrolyte Buffer

The running buffer disclosed in U.S. Pat. No. 5,120,413 (incorporated herein by reference) was utilized for analysis. All chemicals were at least of ACS grade. The electrolyte buffer was made by dissolving 24.72 g of boric acid (MW 61.04; Sigma Chemical Corp., St. Louis, Mo. Product No. B-0252) in 700 ml deionized water; pH was adjusted to 10.0 (±0.25) with 1N NaOH (Aldrich Chemical, Milwaukee, Wis. Product No. 31,95). A final solution of 1000 ml was achieved by the addition of deionized water and the solution was filtered through a 0.22 µm membrane (Corning, Inc., Corning, N.Y. Product No. C/N 25992), followed by storage at room temperature in a glass bottle. The borate buffer had a molarity of 400 mM.

3) Patient Samples

Human blood samples (Physician's Lab Services, Lincoln, Nebr.; Beckman Instrument, Inc.) were collected using Red Top Vacutainer TM collection tubes. After the blood coagulated, the serum was collected and diluted with ICS TM Diluent (Beckman Instruments, Inc., Product No. 663630; comprises 75 mM NaClm 20 mM KPO3, pH 7.0). The serum samples were diluted between 1:10 to 1:50 serum to diluent, based upon the peak ratio of gammaglobulin to albumin—if this ratio was about 1:1, a 1:50 serum: diluent ratio was used; if the peak ratio was about 1:5, a 1:10 serum:diluent ratio was used.

4) Anti-Human Immunoglobulin Antibodies

Rabbit anti-human IgA (DACO Co., Carpinteria, Calif. C/N A092, L/N 035); rabbit anti-human IgM (DACO C/N A426, L/N 030); rabbit anti-lambda bound and free light chain (DACO C/N A191, L/N 020); and rabbit anti-lambda bound and free light chain (DACO C/N A193, L/N 058) were used for coupling with solid phase.

5) Solid Phase

For IgG immunoglobulin, agarose-coupled Protein G (IsoLab, Akron, Ohio C/N IG-1125, L/N 106052) was utilized as the solid phase. For the anti-IgA, anti-IgM, anti-happa and anti-lambda antibodies, cyanogen bromide activated Sepharose TM 4B solid support (Pharmacia, Pascataway, N.Y. C/N 52-1153-AK, L/N NF 04254) was utilized as the solid phase.

B. Methods

1. Solid Phase Preparation

Manufacturer (Pharmacia) instructions were followed. Four batches of Pharmacia CN-Br activated Sepharose 4B solid support were coupled with anti-human IgA, rabbit anti-human IgM, rabbit anti-human happa and rabbit anti-human lambda, respectively, following manufacturer instructions. Briefly, the dried powder solid support was swollen by 1 mM HCl (200 ml/g) for 15 min. 1.0 mg of antibody was dissolved in 1.0 ml of coupling buffer (0.1M NaHCO3, 0.5M NaCl, pH 8.3). 5.0 ml of the dissolved antibody was mixed with 1.0 g of the swollen support. The mixture was placed in a stopped vessel and rotated end-over-end for either 2 hours at room temperature or overnight at 4° C. Excess antibody was washed away with the coupling buffer and remaining active groups were blocked with tris-hydroxymethyl amino methane hydrochloric acid ("TRIS-HCl") (0.1M, pH 8) or ethanolamine (1.0M, pH 9) for 2 hours at room temperature or 16 hours at 4° C., respectively. The gel was washed three times with ICS TM diluent (Beckman Instruments, Inc., Product No. 663630) and 0.1M acetate buffer, pH 4 containing 0.5 NaCl. The antibody coupled gel was stored at 4° C.

The solid phase for IgG analysis was the IsoLab Protein-G coupled agarose.

All solid phase coupled materials were suspended in 50% phosphate buffered saline (pH 7.0); this suspension is referred to herein as "gel slurry."

2. Sample Dilution

30 µl of serum sample was diluted into 300 µl of gel slurry (150 µl of swollen solid phase plus 150 µl phosphate buffered saline). Dilution ratios (serum:gel slurry) was adjusted from between about 1:10 and about 1:100, based upon the protocol dissolved above in Section I.A.3). The preferred ratio is about 1:10.

3. Incubation With Solid Phase

Incubation was accomplished by pipetting the diluted sample:gel slurry mixture for at least 5 excursions. Thereafter, the incubated samples were placed on the inlet tray of the instrument. Care must be taken to avoid uptake of the solid phase by the instrument into the capillary as clogging or erroneous results could occur.

4. Analytical Protocol

Two electropherograms were derived for each sample. Preferably, the first is the "control" and the second is the "immunosubtracted." Normalization of the electropherogram as set forth in detail above, was accomplished by an on-board computer and allows for overlying the two such that subtracted peaks can be readily discerned. By overlaying the normalized control electropherogram, over the normalized immunosubtracted electropherogram; the class or type of monoclonal gammopathy can be readily determined by locating the region where two peaks are not substantially identical in terms of height and width ("substantially" is not intended to be a term of art—the skilled artisan will readily recognize when two peaks are not substantially identical based upon visual inspection.)

II. EXPERIMENTAL RESULTS

A. IgG Monoclonal Gammopathy Sample

Figure 2:
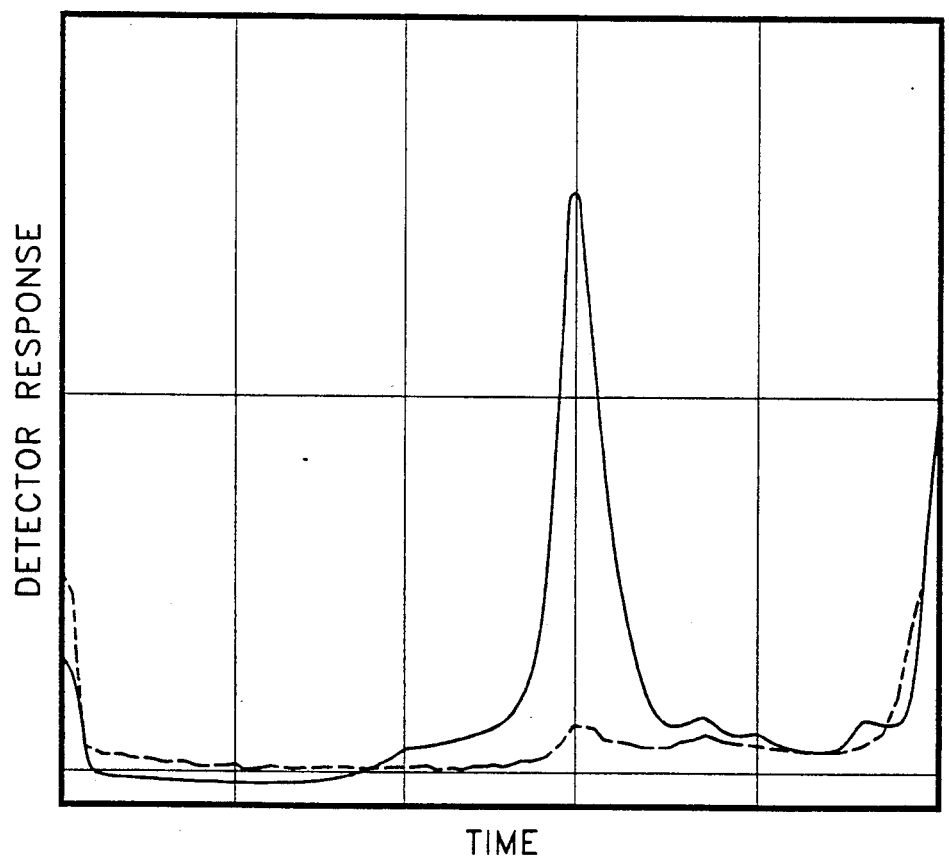
FIG. 2 is an electropherogram derived from Capillary Electrophoretic Immunosubtraction ("CEI") analysis of IgG monoclonal gammopathy patient sample.

Serum sample from an IgG monoclonal gammopathy patient was analyzed using the CEI protocol, whereby a first control analysis was conducted, followed by CEI using insolubilized Protein G. Derived electropherograms were normalized; these are presented in FIG. 2, with the solid line representing the "control" and the dashed line representing the "immunosubtracted." (Unless otherwise indicated, the Figures will utilize this format, i.e. bold line is the electropherogram of the "control" and dashed line is the electropherogram of the "immunosubtraction".) As can be observed, the "immunosubtracted" electropherogram evidences a significant decrease in the peak corresponding to IgG (i.e. the decrease occurred with respect to the sample admixed with insolubilized Protein G).

B. IgA Monoclonal Gammopathy Sample

Figure 3:
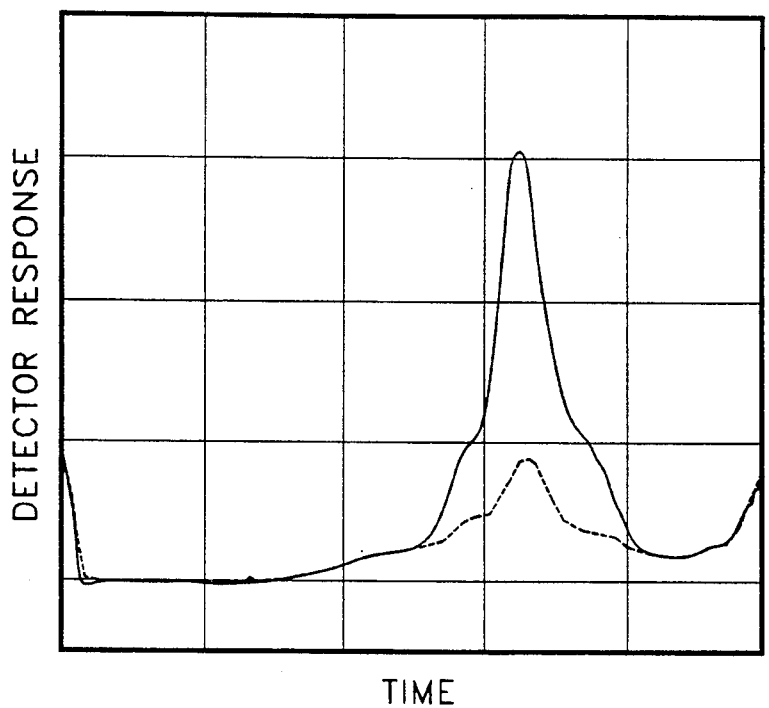
FIG. 3 is an electropherogram derived from CEI analysis of IgA monoclonal gammopathy patient sample.

The CEI protocol was utilized with a serum sample from an individual evidencing IgA monoclonal gammopathy. FIG. 3 provides the normalized electropherograms for both the "control" (bold) and the IgA immunosubtraction utilizing insolubilized anti-IgA antibodies (dashed). A significant decrease in the IgA peak can be observed, indicating the presence of IgA monoclonal gammopathy in the sample.

C. Lambda Light Chain Monoclonal Gammopathy Sample

Figure 4:
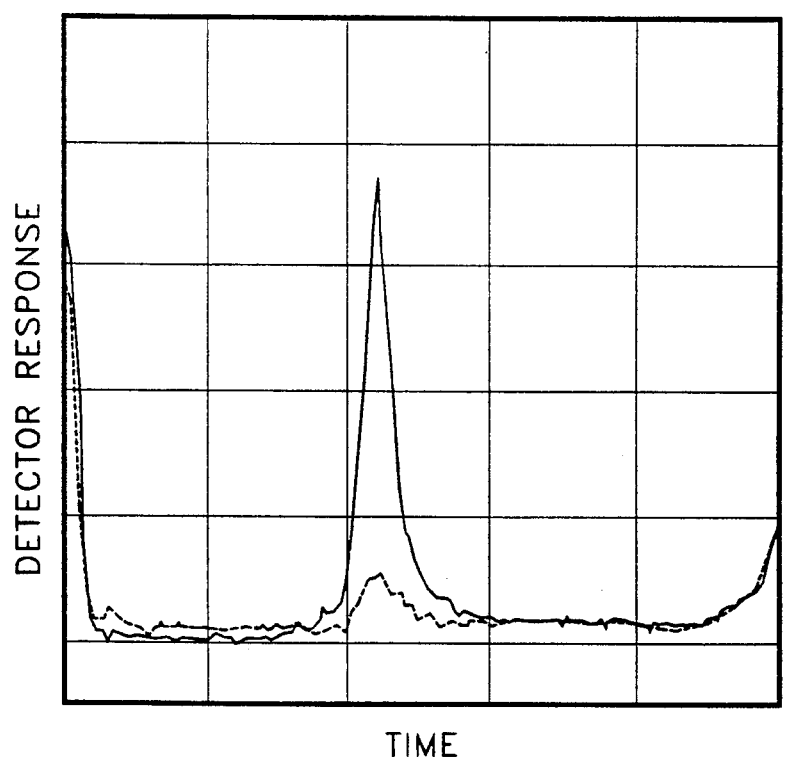
FIG. 4A of 4B are electropherograms derived from CEI analysis of the same lambda light chain monoclonal gammopathy patient sample, with 4A being derived from utilization of insolubilized anti-lambda antibodies and 4B being derived from utilization of insolubilized anti-kappa antibodies.
Figure 5:
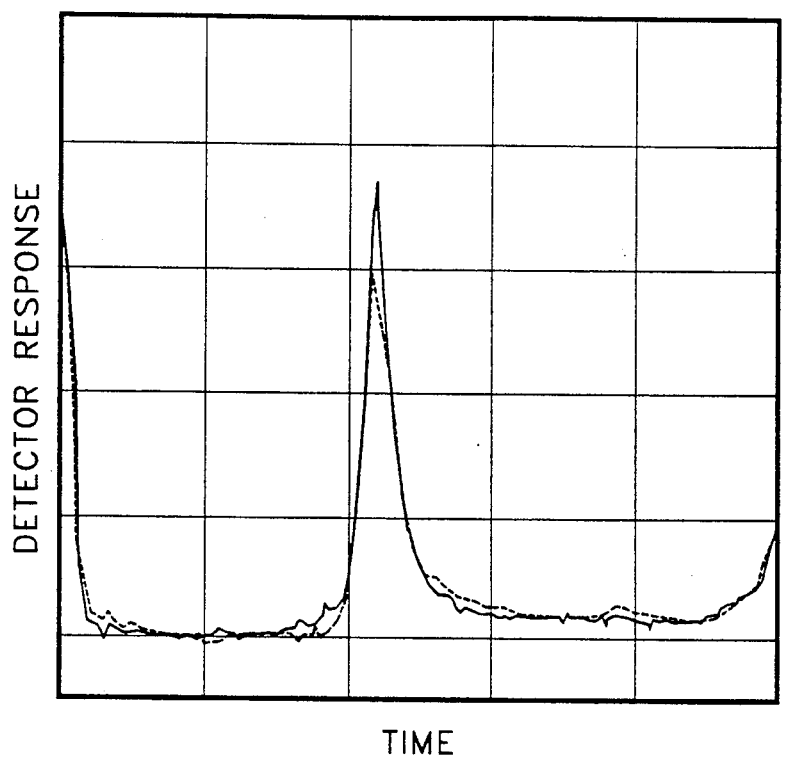
FIG. 5A, 5B, 5C, 5D and 5E are electropherograms derived from CEI analysis of the same IgG lambda monoclonal gammopathy patient sample, with 5A being derived from utilization of insolubilized Protein G; 5B from insolubilized anti-IgA antibodies; 5C from insolubilized anti-IgM antibodies 5D from insolubilized anti-kappa antibodies; and 5E from insolubilized anti-lambda antibodies.
Figure 6:
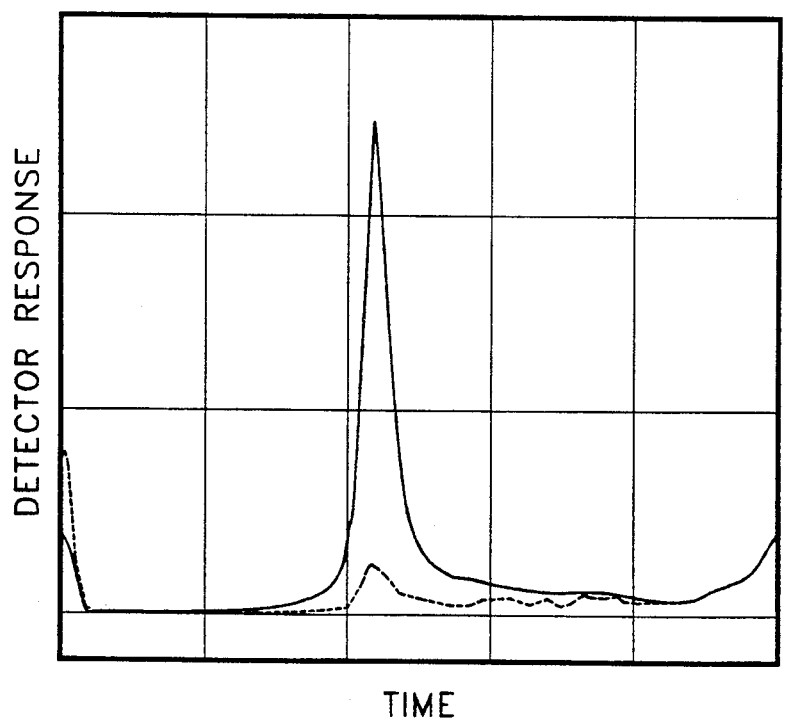
Figure 7:
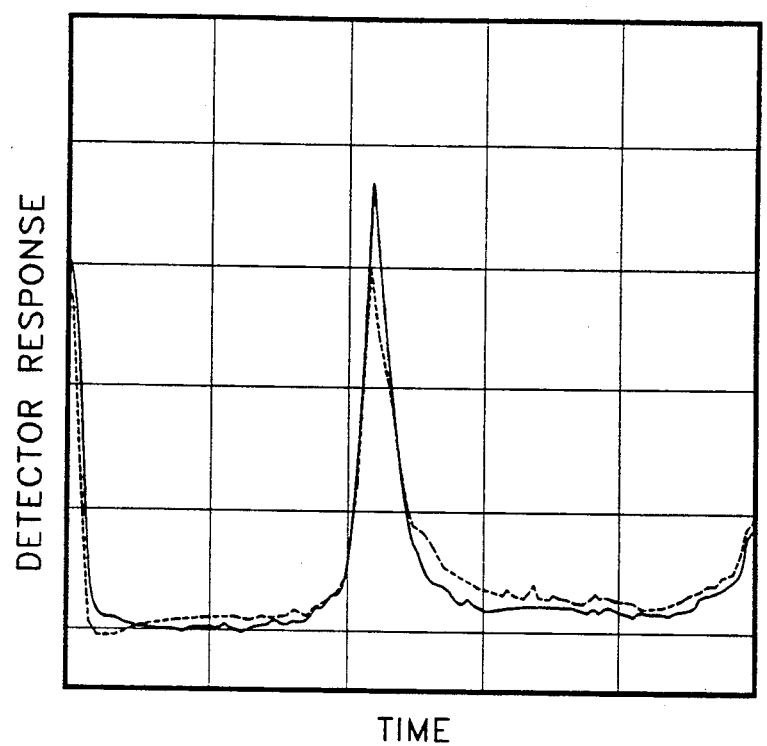
Figure 8:
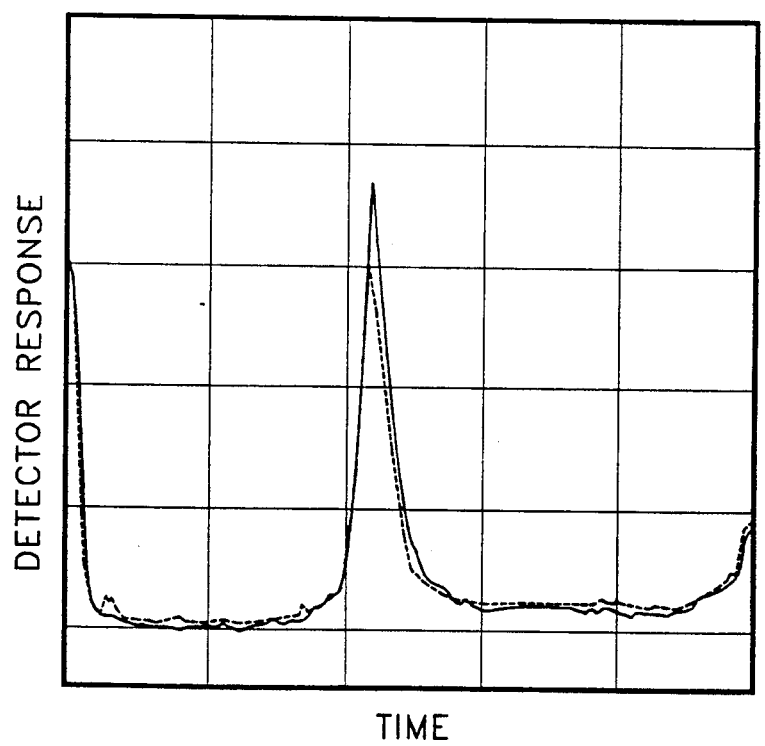
Figure 9:
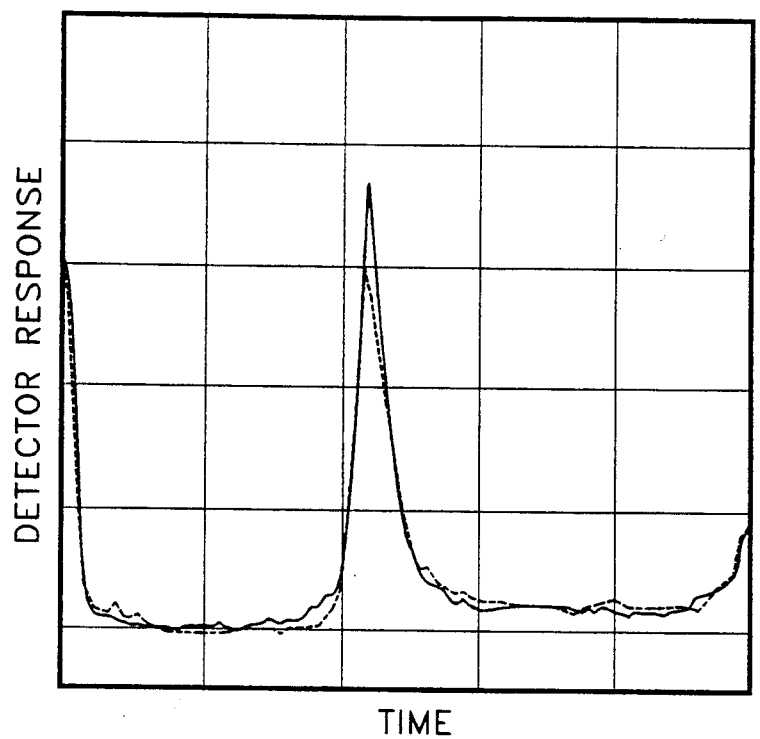
Figure 10:
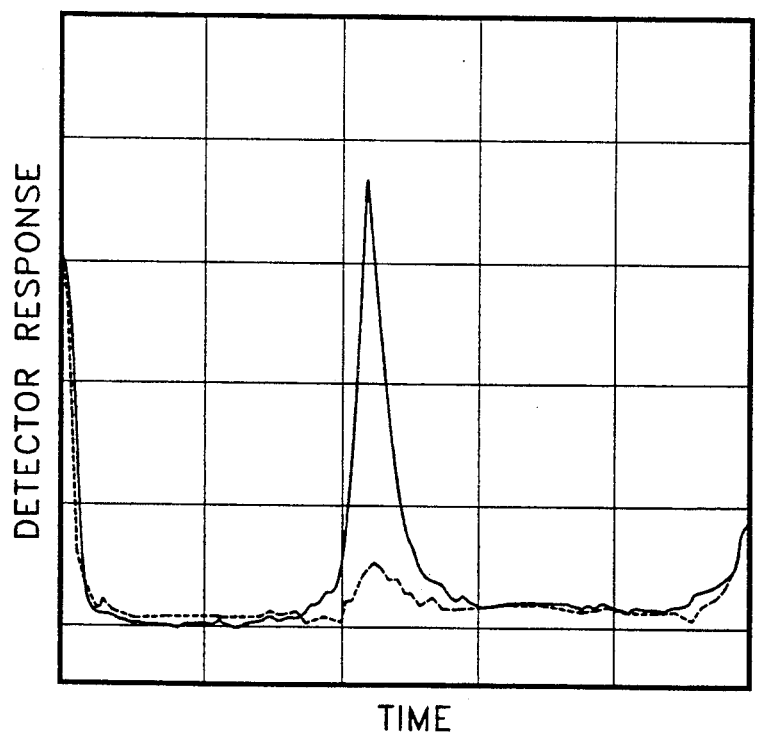

FIGS. 4A and 4B represent CEI electropherograms derived from the sample from an individual evidencing lambda light chain monoclonal gammopathy. In FIG. 4A, the immunosubtracted portion of the normalized electropherograms was derived using insolubilized anti-kappa antibodies admixed with the sample—as would be expected with such a protocol, the two electropherograms of FIG. 4A are substantially identical. In FIG. 4B, the immunosubtracted portion of the normalized electropherograms was derived using insolubilized anti-lambda antibodies admixed with the sample. The CEI electropherograms of FIG. 4B are consistent with the specific monoclonal gammopathy of the patient sample.

D. IgG-Lambda Light Chain Gammopathy Sample

Serum sample from an individual evidence IgG-Lambda Light Chain Gammopathy was analyzed by CEI using five different conditions: (A) insolubilized Protein G admixed with sample; (B) insolubilized anti-IgA antibodies; (C) insolubilized anti-IgM antibodies; (D) insolubilized anti-kappa antibodies; and (E) insolubilized anti-lambda antibodies. The electropherograms of FIGS. 5A-E provide normalized control and immunosubtracted profiles of the foregoing five conditions, respectively. As is evident from FIGS. 5A-E, only two of the five conditions provide significantly decreased peaks—the sample admixed with insolubilized Protein G and the sample admixed with insolubilized anti-lambda antibodies. I.e., based upon the five normalized electropherograms, the data indicates that the sample was obtained from a patient evidencing IgA-Lambda gammopathy, as is consistent with the actual clinical history of the patient.

The foregoing evidences the utility of Capillary Electrophoretic Immunosubtraction. Because of the speed, accuracy and small sample volume associated with capillary electrophoresis, CEI is an efficient protocol for analyzing, inter alia, monoclonal gammopathies. As will be apparent to those in the art, CEI can also be utilized as a validation protocol. E.g., using insolubilized antibody to a particular analyte of interest, normalized control and immunosubtracted electropherograms can be utilized to identify with precision not only the presence of the analyte, but also the relative location of such analyte along the electropherogram.

While the foregoing Examples are directed to seriatim analysis of the samples, those in the art will recognize that multichannel instruments can be utilized to simultaneously derive the control and immunosubtracted results. Either protocol is satisfactory; however, it is preferred that in a clinical setting these analyses be conducted simultaneously. Accordingly, the foregoing Examples, are not to be construed as limiting the protocol to seriatim sample analysis. Additionally, while the foregoing Examples utilize a particular capillary electrophoresis system, neither the disclosure nor claims are limited thereto.

While the foregoing has been described in considerable detail, it is to be understood that the foregoing description and drawings of preferred embodiments are not to be construed as limiting the disclosure or the claims to follow. Modifications which are within the purview of those skilled in the art are included within the scope of the disclosure and the claims to follow.

What is claimed is:

1. A method for the capillary electrophoretic analysis of a sample comprising at least one consistent part comprising the steps of:
   (a) separating a portion of a first aliquot of the sample into constituent parts by capillary electrophoretic techniques, and detecting said parts;
   (b) admixing a second aliquot of said sample with at least one specific binding partner to a constituent part of said sample, said specific binding partner capable of being substantially removed from said aliquot;
   (c) separating a portion of said second aliquot into constituent parts by capillary electrophoretic technique, and detecting said parts; and,
   (d) comparing the separated constituent parts of step (c) with the separated constituent parts of step (a).

2. The method of claim 1 wherein said sample is selected from the group consisting of whole blood, plasma, serum, urine and cerebrospinal fluid.

3. The method of claim 1 wherein the separating of steps (a) and (c) are conducted simultaneously.

4. The method of claim 1 wherein the detected constituent parts of step (a) and (c) are normalized.

5. The method of claim 1 wherein the ratio of specific binding partner to said constituent is between about 1:1 and about 1:15.

6. The method of claim 1 wherein said specific binding partner comprises a substance capable of binding to an insolubilized material.

7. The method of claim 1 wherein said specific binding partner is insolubilized.

8. The method of claim 1 wherein said constituent is a human immunoglobulin.

9. A method for the capillary elecetrophoretic analysis of a sample comprising at least one constituent part comprising the steps of:
   (a) simultaneously separating: a portion of a first aliquot of the sample into constituent parts by capillary electrophoretic techniques, and detecting said parts; and a portion of a second aliquot of the sample into constituent parts, the second aliquot having been admixed with at least one specific binding partner to a constituent of said sample, said binding partner capable of being substantially removed from the second aliquot; and, (b) comparing the separated constituent parts of the first aliquot with the separated constituent parts of the second aliquot.

10. The method of claim 9 wherein said constituent is a human immunoglobulin.

11. The method of claim 10 wherein the specific binding partner is an anti-human immunoglobulin antibody.

12. The method of claim 11 wherein the ratio of anti-human immunoglobulin antibody to human immunoglobulin is between 1:1 and about 1:15.

13. The method of claim 9 wherein said specific binding partner is insolubilized.

14. A method for the capillary electrophoretic analysis of a clinical sample comprising at least one human immunoglobulin, comprising the steps of:

(a) separating a portion of a first aliquot of the clinical sample into constituent parts by capillary electrophoretic techniques, and detecting said parts:

(b) admixing an insolubilized anti-human immunoglobulin antibody specific for said human immunoglobulin with a second aliquot of said clinical sample and separating a portion of said aliquot not comprising said insolubilized anti-human immunoglobulin antibody into constituent parts by capillary electrophoretic techniques, and detecting said parts; and, (c) comparing the separated constituent parts of step (b) with the separated constituent parts of step (a).

15. The method of claim 14 wherein step (a) and step (b) are performed simultaneously.

16. The method of claim 14 wherein the ratio of said anti-human immunoglobulin antibody to said human immunoglobulin is between about 1:1 and about 1:15.

17. The method of claim 14 wherein said clinical sample is selected from the group consisting of whole blood, plasma, serum, urine and cerebrospinal fluid.

* * * * *